United States Patent [19]

Kikuchi et al.

[11] Patent Number: 5,238,964
[45] Date of Patent: Aug. 24, 1993

[54] AGENT FOR TREATMENT OF CEREBROVASCULAR CONTRACTION

[75] Inventors: Haruhiko Kikuchi, Suita; Hiroji Yanamoto, Kyoto, both of Japan

[73] Assignee: Torii & Co., Ltd., Tokyo, Japan

[21] Appl. No.: 835,744

[22] Filed: Feb. 13, 1992

Related U.S. Application Data

[63] Continuation-in-part of Ser. No. 7,670,456, Mar. 12, 1991, abandoned, which is a continuation-in-part of Ser. No. 7,615,250, Nov. 19, 1990, abandoned.

[30] Foreign Application Priority Data

Apr. 5, 1990 [JP] Japan .................................. 2-090682

[51] Int. Cl.[5] .................... A61K 31/155; A61K 31/36
[52] U.S. Cl. .................................. 514/634; 514/466
[58] Field of Search ............... 514/634, 358, 466, 522, 514/540; 540/522

[56] References Cited

U.S. PATENT DOCUMENTS

| | | | |
|---|---|---|---|
| 4,454,338 | 6/1984 | Fujii et al. | 560/34 |
| 4,490,388 | 12/1984 | Fujii et al. | 424/278 |
| 4,496,584 | 1/1985 | Fujii et al. | 514/510 |
| 4,514,416 | 4/1985 | Fujii et al. | 549/442 |
| 4,532,255 | 7/1985 | Fujii et al. | 514/466 |
| 4,563,527 | 1/1986 | Fujii et al. | 540/107 |
| 4,570,006 | 2/1986 | Fujii et al. | 549/442 |
| 4,634,783 | 1/1987 | Fujii et al. | 549/475 |
| 4,777,182 | 10/1988 | Fujii et al. | 514/392 |
| 4,820,730 | 4/1989 | Fujii et al. | 514/510 |

FOREIGN PATENT DOCUMENTS

0048433 3/1982 European Pat. Off. .
0229370 6/1985 European Pat. Off. .

OTHER PUBLICATIONS

Akizawa, T., et al., "Comparative Clinical Trial of Regional Anticoagulation for Hemodialysis", *Trans. Am. Soc. Artif. Intern. Organs* (1988), vol. 34, pp. 176-178.
Kreil, E., et al., "Nafamstat mesilate attenuates pulmonary hypertension in heparin-protamine reactions", *J. Appl. Physiol.* (1989), vol. 67, pp. 1463-1471.
Chemical Abstracts, vol. 109(26), abstract no. 236965p (1988).

Primary Examiner—Frederick E. Waddell
Assistant Examiner—T. J. Criares
Attorney, Agent, or Firm—Beveridge, DeGrandi, Weilacher & Young

[57] ABSTRACT

A method for the treatment of cerebrovascular contraction in mammals involving administration of a pharmaceutical composition containing as an effective ingredient a p-guanidinobenzoic acid derivative represented by the formula

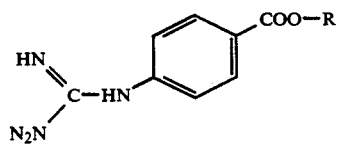

wherein R denotes a group represented by the formula

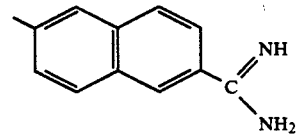

or a pharmaceutically acceptable salt thereof, and a pharmaceutically acceptable carrier.

8 Claims, No Drawings

AGENT FOR TREATMENT OF CEREBROVASCULAR CONTRACTION

REFERENCE TO A RELATED APPLICATION

The present application is a continuation-in-part of our copending U.S. patent application Ser. No. 07/670,456, filed on Mar. 12, 1991, now abandoned, which is incorporated by reference in its entirety, which is a continuation-in-part of our copending U.S. patent application Ser. No. 07/615,250 filed Nov. 18, 1990 now abandoned.

BACKGROUND OF THE INTRODUCTION

The present invention relates to a medicinal composition effective for the treatment of cerebrovascular contraction caused by subarachnoid bleeding, etc. The present invention also relates to a method of treating cerebrovascular contraction utilizing such a medicinal composition.

Subarachnoid bleeding occurs in about 12 persons per population of 100,000. About 50% of the patients will die or become disabled at the first attack and, if the patients receive no medical treatment, a further 25–30% thereof will die due to rebleeding.

Treatments commonly given at the onset of subarachnoid bleeding include rest in bed, control of blood pressure, administration of analgesics and sedatives, administration of hemostatic agents, control of encephalic pressure, and surgery.

At the subacute stage, further cerebrovascular contraction takes place in about 40% of the patients. The cerebrovascular contraction at the subacute stage ranks second to rebleeding in importance as regards the prognosis of the patient. That is, the prognosis of the patient is greatly influenced by how well the cerebrovascular contraction can be suppressed after subarachnoid bleeding. No agent is known at present which can prevent or treat said cerebrovascular contraction. Accordingly, an agent which can prevent and/or treat cerebrovascular bleeding has been eagerly desired.

SUMMARY OF THE INVENTION

A method for the treatment of cerebrovascular contraction in mammals is disclosed which involves administration of a pharmaceutical composition containing as an effective ingredient a p-guanidinobenzoic acid derivative represented by the formula

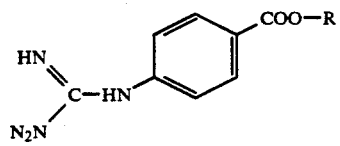

wherein R denotes a group represented by the formula

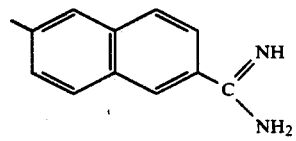

or a group represented by the formula

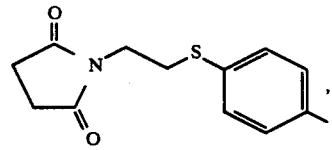

or a pharmaceutically acceptable salt thereof, and a pharmaceutically acceptable carrier.

DETAILED DESCRIPTION OF THE INVENTION

Compounds represented by the formula

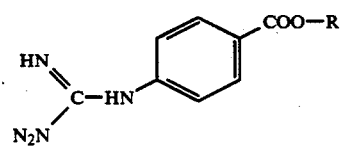

wherein R denotes a group represented by the formula

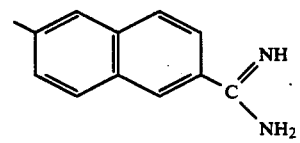

or a group represented by the formula

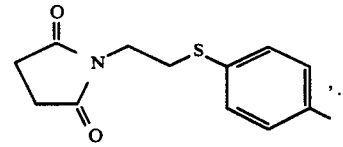

are already known and are in use for the purpose of treating pancreatitis. They are agents whose safety, and effectiveness in treating pancreatitis, are already known. However, it has not been know that these agents are effective in controlling cerebrovascular bleeding.

The present inventors have made extensive study to develop a pharmaceutical composition which is effective in controlling cerebrovascular contraction subsequent to subarachnoid bleeding. As the result it has been found out that the compound represented by the formula

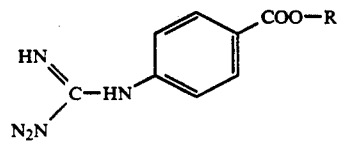

wherein R denote a group represented by the formula

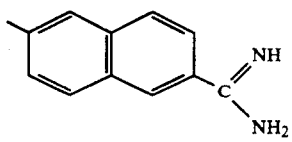

or a group represented by the formula

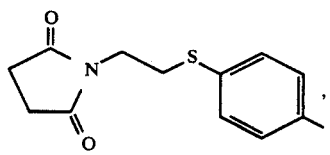

or a pharmaceutically acceptable salt thereof, and a pharmaceutically acceptable carrier, markedly improves the condition of cerebrovascular contraction occurring subsequent to subarachnoid bleeding.

The compound represented by the above formula may be administered by any methods conventionally used for the administration of medicinal agents, including injection and drip (intravenous) administration. In an urgent need, however, it is desirably administered by intravenous injection.

The pharmaceutical compositions of this invention may contain the active compounds together with a solid or liquid pharmaceutically acceptable nontoxic carrier. Such pharmaceutical carriers can be sterile liquids, such as water. Water is a preferred carrier when the pharmaceutical composition is administered intravenously. Saline solution and aqueous dextrose and glycerol solutions can also be employed as liquid carriers, particularly for injectable solutions. Suitable pharmaceutical excipients include glucose, lactose, sucrose, D-mannitol, sodium chloride, water, and the like. These compositions can take the form of solutions, suspensions, capsules, powders (e.g., lyophilized), sustained-release formulations and the like. Suitable pharmaceutical carriers are described in "Remington's Pharmaceutical Sciences" by E. W. Martin. Such compositions will contain an effective therapeutic amount of the active compound together with a suitable amount of carrier so as to provide the form for proper administration to the host. While intravenous injection is a very effective form of administration, other modes can be employed.

The present invention will be described in detail below with reference to the following examples:

By injecting previously collected blood into the postcisterna of a rabbit, subarachnoid bleeding similar to human subarachnoid bleeding can be produced experimentally in the rabbit. The therapeutic effect of a pharmaceutical composition for treating cerebrovascular contraction is judged by comparing the thickness of the basal arteria before and after the experimental production of subarachnoid bleeding.

EXAMPLE 1

Subarachnoid bleeding was produced experimentally in rabbits, and 20 minutes thereafter 3 mg, 6 mg and 9 mg of 6-amidino-2-naphthyl p-guanidinobenzoate dimethanesulfonate

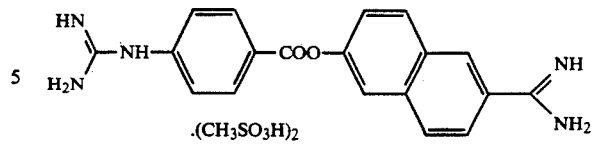

were respectively administered intravenously to the rabbits.

The ratios of the thickness of the basal arteria before subarachnoid bleeding to that after subarachnoid bleeding are shown in the following Table.

TABLE

Effect of 6-amidino-2-naphthyl p-guanidinobenzoate dimethanesulfonate on experimental subarachnoid bleeding

| Dosage | Basal arteria thickness ratio (%)* | | | | |
|---|---|---|---|---|---|
| | 1st day | 2nd day | 3rd day | 4th day | 5th day |
| 0 mg/kg | 73 | 65 | 71 | 78 | 84 |
| 3 mg/kg | 86 | 79 | 85 | 88 | 90 |
| 6 mg/kg | 97 | 95 | 95 | 96 | 101 |

Note:
*Ratio of the thickness of basal arteria after subarachnoid bleeding to that before subarachnoid bleeding The results shown in the Table above reveal that 6-amidino-2-naphthyl p-guanidinobenzoate dimethanesulfonate has clearly suppressed the cerebrovascular contraction subsequent to subarachnoid bleeding.

EXAMPLE 2

An experiment was performed in the same manner as in Example 1 except that 4-(2-succinimidoethylthio)-phenyl 4-guanidinobenzoate methanesulfonate

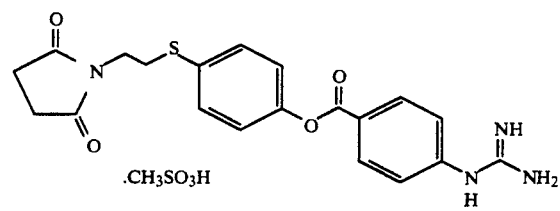

was used in place of 6-amidino-2-naphthyl p-guanidinobenzoate dimethanesulfonate. It was found that said compound also clearly suppressed the cerebrovascular contraction subsequent to subarachnoid bleeding, showing the same effect as that of the compound used in Example 1.

EXAMPLE 3

We have tried intermittent intravenous administration of FUT-175 (nafamostat mesilate, the present compound) for the purpose of prevention and/or treatment of cerebrovascular contraction after acute phase operation on subarachnoid bleeding patients. A dosage of 40-160 mg/day was chosen by converting the amount of drug per kg rabbit weight to amount of drug per kg of human weight.

The subjects were the ruptured cerebral aneurysm patients who had acute phase operation and belonged to Group 3 or 4 in Fisher's preoperative CT classification (Fisher, C. M., et al., "Cerebral vasospasm with ruptured saccular aneurysm-Clinical manifestations" (1977), Neurosurgery, volume 1, pages 245-248). In Group 3, the patients who were observed to have 3 mm or greater thick clot layers at three or more cisterns were selected; and in Group 4, the patients whose main trouble was intracerebral hematoma were excluded. Also, the subjects were limited to the cases of Grades II-IV in Hunt and Hess gravity grating without modification by previous history and to the patients to whom administration could be started within 48 hours after crisis (Hunt, W. E., et al., "Surgical risk as related to time of intervention in the repair of intracranial aneurysms" (1968), J. Neurosurg., volume 28, pages 14-20).

The compound was given to the subjects by intermittent intravenous administration starting immediately after operation. In Group A, the compound was administered twice a day, 20 mg per administration (40 mg in total daily dosage) for 4 days; four times a day, 20 mg per administration (80 mg in total daily dosage) for 4 days in Group B; and four times a day, 40 mg per administration (160 mg in total daily dosage) for 4 days in Group C. Each dose of the compound was dissolved in 100 ml of physiological saline. Time of one intravenous administration was normally 2 hours.

The control cases were the serious subarachnoid bleeding patients after acute phase clipping operation performed in our clinic in 1989. The control group comprised 22 cases and the treated group 23 cases (as shown in Table 1). Both groups were substantially commensurate with each other in gravity grating and CT classification (Fisher classification by computed tomography), but in the control group there were slightly more cases of mycotic cerebral aneurysm than in the treated group.

There was no difference between the control and treated groups in substances of treatment excepting administration of the present compound and in operating staff. The effect of the treatment was judged by occurrence or non-occurrence of delayed ischemic neurological deficit (DIND), low-density CT area due to vasospasm and caliber change in arteries as observed by cerebral angiography conducted in the period from day 5 to day 8 (post occurrence of cerebrovascular contraction) which is considered the peak period of development of vasospasm.

For judgement of spasm in the control group, an Angiographic Spasm Scale (ASS) of the following grading was prepared:

Grade 0 (none): No caliber change in any arteries,
Grade 1 (mild): Vascular contraction is localized,
Grade 2 (moderate): Multisegmental vascular contraction is observed, and
Grade 3 (severe): Severe contraction exceeding 50% is seen in multisegmental sites (Weir, B., et al., "Time course of vasospasm in man" (1978), J. Neurosurg., volume 48, pages 173-178; Kim, H., et al., "Time course of vasospasm—Its clinical significance" (1979), Neuro. Med. Chir. (Tokyo), volume 19, pages 95-102).

The Glasgow Outcome Scale (GOS) was used to evaluate the outcome one month after crisis. According to GOS, there are five degrees: 1-death, 2-vegetative state, 3-severe disability, 4-moderate disability, 5-good recovery.

The results from Groups A, B and C are shown in Table 2 (* indicates no data).

In Group A, where the compound was administered at a daily dosage of 40 mg for 4 days, incidence of DIND and CT-low attributable thereto were seen in 2 out of 9 cases. In spasm grading, 3 cases were at grade 1 of ASS, 3 cases at grade 2, and 3 cases at grade 3.

In Group B, as a result of 4-day administration of the compound at a daily dosage of 80 mg, DIND was admitted in one out of 9 cases and there was no case which showed a low density area on CT scan. Regarding spasm grading, there were 4 cases at grade 0: no caliber change in any arteries, 3 cases at grade 1, and one case at grade 3. Incidence of DIND was seen only in the case who underwent re-operation on day 5 to remove the remaining hematoma.

In Group C comprising 5 cases of 4-day administration at a daily dosage of 160 mg, there was no case which incurred DIND. The number 2 case had operation for removal of epidural hematoma but showed no sign of DIND. 4 out of 5 cases were found good in GOS (Glasgow Outcome Scale).

In sum, regarding the degree of cerebrovascular contraction measured according to angiographic spasm grading in treated groups A, B and C, 64% of the subjects had no change or were mild in degree of contraction (as shown in Table 3). It is to be noted that in Groups B and C, which had higher dosage of the compound, 85% of the subjects were mild or none in degree of contraction. On the other hand, ASS Grade 3 (severe) was seen in 18% of the subjects in Groups A, B and C combined, and only 8% of the total subjects in Groups B and C where the compound was administered at higher dosage.

As shown in Table 4, DIND was admitted in 55% of the subjects and CT low due to spasm was noted in 43% of the subjects in the Control Group; whereas in Groups A, B and C, where all the subjects had treatment with the present compound, incidence of DIND dropped to 13% and CT low was down to 9%, and they were further improved to 7% and 0%, respectively, in Groups B and C where dosage of the present compound administered was high. Also, according to the Glasgow Outcome Scale one month after crisis, 36% of the subjects showed good recovery and another 36% fell under the section of vegetative survival+death in the Control Group; whereas in Groups A, B and C the percentage of the subjects who showed good recovery rose to 65% while vegetative survival+death dropped to 9%, and further improvements were achieved, registering 71% and 0%, respectively, in Groups B and C where the compound was administered at higher dosage.

The present compound is a serine protease inhibitor which can inhibit various kinds of serine protease including C 1r, C 1s, factor B and factor D of complement system, factor XIIa, factor Xa and thrombin of coagulation system, plasma kallikrein of quinine system, plasmin of fibrinolytic system, trypsin, etc. That is, the present compound inhibits inflammation reactions originating in plasma protein which advance under the action of said serine proteases. It is also known that the present compound has concentration dependent platelet agglutination inhibiting action, but its half-life period in blood is short (1.1 minute in α phase and 23.1 minutes in β phase) and it quickly passes into tissue. It was considered that the administration method employed in this experiment would give no influence on circulating blood coagulating action of the compound. Actually, bleeding time, coagulation time, prothrombin time (PT) and activated partial thromboplastin time (APTT) measured during intravenous administration of the compound in the treated groups B and C were all in the normal ranges, and no significant extension by administration of the present compound was admitted. As the present compound could inhibit incidence of delayed ischemic neurological deficit caused by cerebrovascular contraction after serious subarachnoid bleeding and also improve the prognosis of the patient, it is expected that acute phase use of this protease inhibitor would become an effective measure for treatment of cerebrovascular contraction.

An effective amount of the p-guanidinobenzoic acid derivative is that amount which successfully treats cerebrovascular contraction in a mammal, generally 40 to 160 mg per day for four days.

U.S. Pat. No. 4,454,338 is incorporated by reference in its entirety, especially for disclosure of pharmaceutically acceptable salts.

Further variations and modifications of the invention will become apparent to those skilled in the art from the foregoing and are intended to be encompassed by the claims appended hereto.

What is claimed:

1. A method of treating cerebrovascular contraction in a mammal in need of such treatment, comprising administering to said mammal a pharmacologically effective amount of a pharmaceutical composition comprising a p-guanidinobenzoic acid derivative represented by the formula

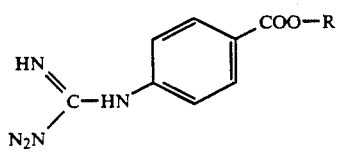

wherein R denotes a group represented by the formula

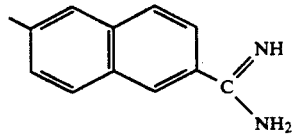

or a pharmaceutically acceptable salt thereof, and a pharmaceutically acceptable carrier.

2. The method according to claim 1, wherein said pharmacologically effect amount of said pharmaceutical composition is 40 to 160 mg/day administered intravenously.

3. The method according to claim 2, wherein 20 mg of said pharmaceutical composition is administered twice a day.

4. The method according to claim 3, wherein 20 mg of said pharmaceutical composition is administered twice a day for four days.

5. The method according to claim 2, wherein 20 mg of said pharmaceutical composition is administered four times a day.

6. The method according to claim 5, wherein 20 mg of said pharmaceutical composition is administered four times a day for four days.

7. The method according to claim 2, wherein 40 mg of said pharmaceutical composition is administered four times a day.

8. The method according to claim 7, wherein 40 mg of said pharmaceutical composition is administered four times a day for four days.

* * * * *